(12) United States Patent
Yang et al.

(10) Patent No.: US 7,678,260 B1
(45) Date of Patent: Mar. 16, 2010

(54) MEASUREMENT OF CUMULATIVE LOCALIZED CORROSION RATE USING COUPLED MULTIELECTRODE ARRAY SENSORS

(76) Inventors: Lietai Yang, 11215 Jade Spring, San Antonio, TX (US) 78249; Xiaodong Sun Yang, 11215 Jade Spring, San Antonio, TX (US) 78249

(*) Notice: Subject to any disclaimer, the term of this patent is extended or adjusted under 35 U.S.C. 154(b) by 462 days.

(21) Appl. No.: 11/703,275

(22) Filed: Feb. 7, 2007

Related U.S. Application Data (60) Provisional application No. 60/771,332, filed on Feb. 8, 2006.

(51) Int. Cl.
*G01N 17/04* (2006.01)

(52) U.S. Cl. ............... 205/775.5; 204/404; 324/71.2; 324/700

(58) Field of Classification Search ............. 205/775, 205/775.5; 204/404; 324/71.2, 693, 700
See application file for complete search history.

(56) References Cited

U.S. PATENT DOCUMENTS

| | | | |
|---|---|---|---|
| 6,132,593 | A | 10/2000 | Tan |
| 6,683,463 | B2 | 1/2004 | Yang et al. |
| 6,987,396 | B2 | 1/2006 | Yang et al. |

OTHER PUBLICATIONS

L. Yang and N. Sridhar, "Coupled Multielectrode Online Corrosion Sensor," Materials Performance, 2003, September issue, p. 48.

L. Yang, N. Sridhar, O. Pensado and D. Dunn, "An In-situ Galvanically Coupled Multi-Electrode Array Sensor for Localized Corrosion", Corrosion, 58, p. 1004, 2002.

Lietai Yang, Darrell Dun and Gustavo Cragnolino, "An Improved Method for Real-time and Online Corrosion Monitoring Using Coupled Multielectrode Array Sensors," Corrosion/2005, paper No. 05379, (Houston, TX: Nace International, 2005).

Xiaodong Sun and Lietai Yang, "Real-Time Monitoring of Localized and General Corrosion Rates in Simulated Marine Environments Using Coupled Multielectrode Array Sensors," Corrosion/2006, paper No. 06284 (Houston, TX: Nace, 2006).

Lietai Yang and Xiaodong Sun, "Measurement of Cumulative Localized Corrosion Rate Using Coupled Multielectrode Array Sensors," Corrosion/2007, paper No. 07378 (Houston, TX: Nace, 2007).

*Primary Examiner*—Kay K Olsen (57) ABSTRACT

Methods of deriving the cumulative maximum localized corrosion rate and cumulative localized corrosion rate factor for corrosion monitoring using coupled multielectrode array sensor probes are disclosed. Compared with maximum localized corrosion rate, which is derived from the corrosion rate on any of the electrodes of a probe that has the highest corrosion rate at a given moment of time, cumulative maximum localized corrosion rate is derived from the corrosion rate of the electrode that has been corroded the most in a given time period. The cumulative maximum localized corrosion rate is directly related to the corrosion damage (maximum localized corrosion depth); the maximum localized corrosion depth equals the integration of the cumulative maximum localized corrosion rate. Cumulative maximum localized corrosion rate should be used to evaluate the localized corrosion effect on metal damage.

5 Claims, 12 Drawing Sheets

MEASUREMENT OF CUMULATIVE LOCALIZED CORROSION RATE USING COUPLED MULTIELECTRODE ARRAY SENSORS

RELATED PATENT APPLICATION

This application claims the benefit of U.S. Provisional Application No. 60/771,332, filed Feb. 8, 2006, by Lietai Yang and Xiaodong Sun Yang, entitled "Measurement of Cumulative Localized Corrosion Rate Using Coupled Multielectrode Array Sensors."

TECHNICAL FIELD OF THE INVENTION

This invention relates to methods for deriving localized corrosion parameters for corrosion monitoring, using multielectrode sensors.

BACKGROUND OF THE INVENTION

Coupled multielectrode array sensors (see U.S. Pat. No. 6,683,463 and No. 6,132,593) have been used for corrosion monitoring and electrochemical studies (see L. Yang and N. Sridhar, "Coupled Multielectrode Online Corrosion Sensor," Materials Performance, 2003, September issue, page 48). The present invention is related to how one can derive a more meaningful localized corrosion rate using the concept of multielectrode electrochemical devices or corrosion sensors.

DETAILED DESCRIPTIONS OF THE INVENTION

Overviews

Figure 1:
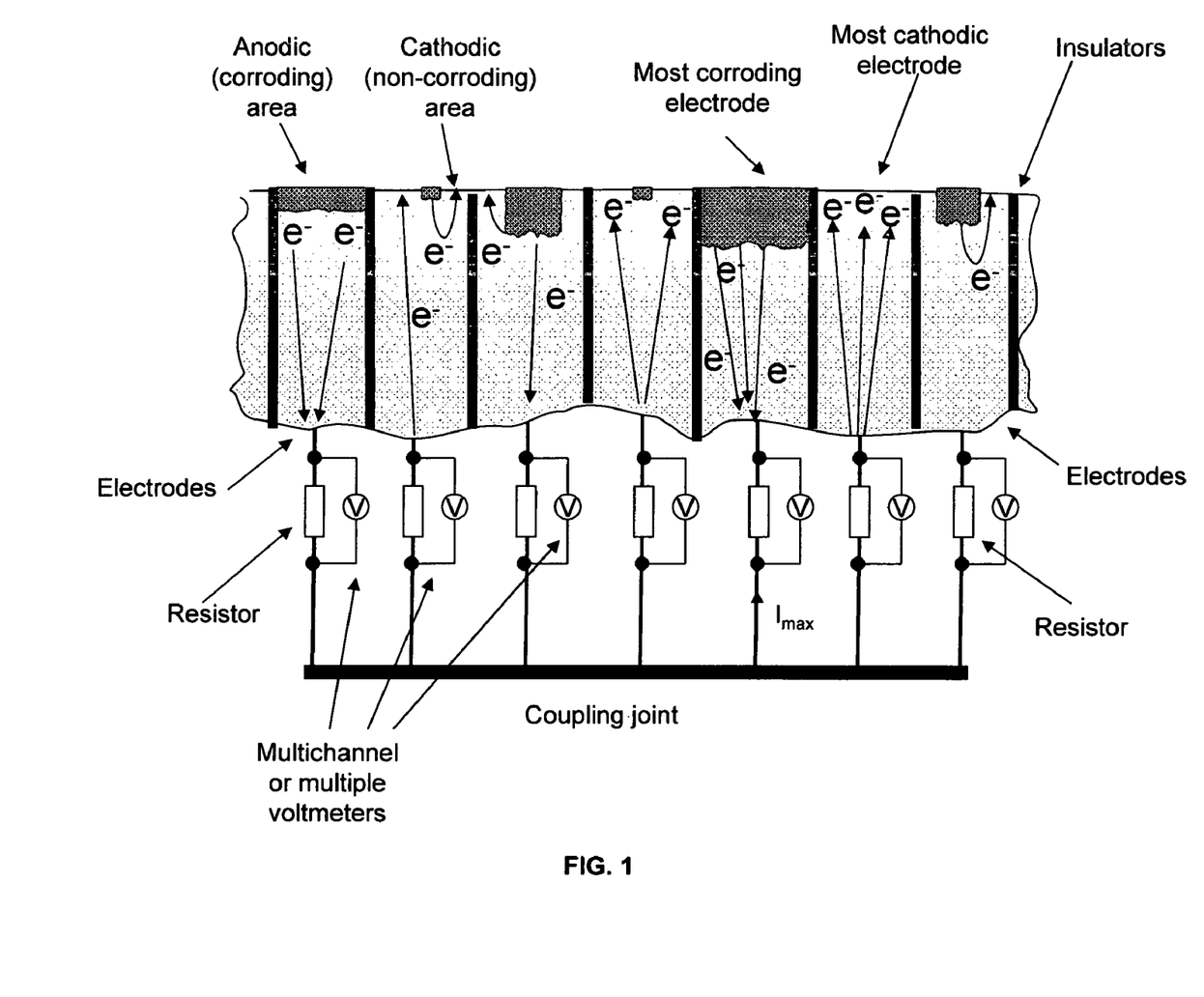
FIG. 1 illustrates the principle of a coupled multielectrode array sensor using resistors and voltmeters to measure the coupling currents.
Figure 2:
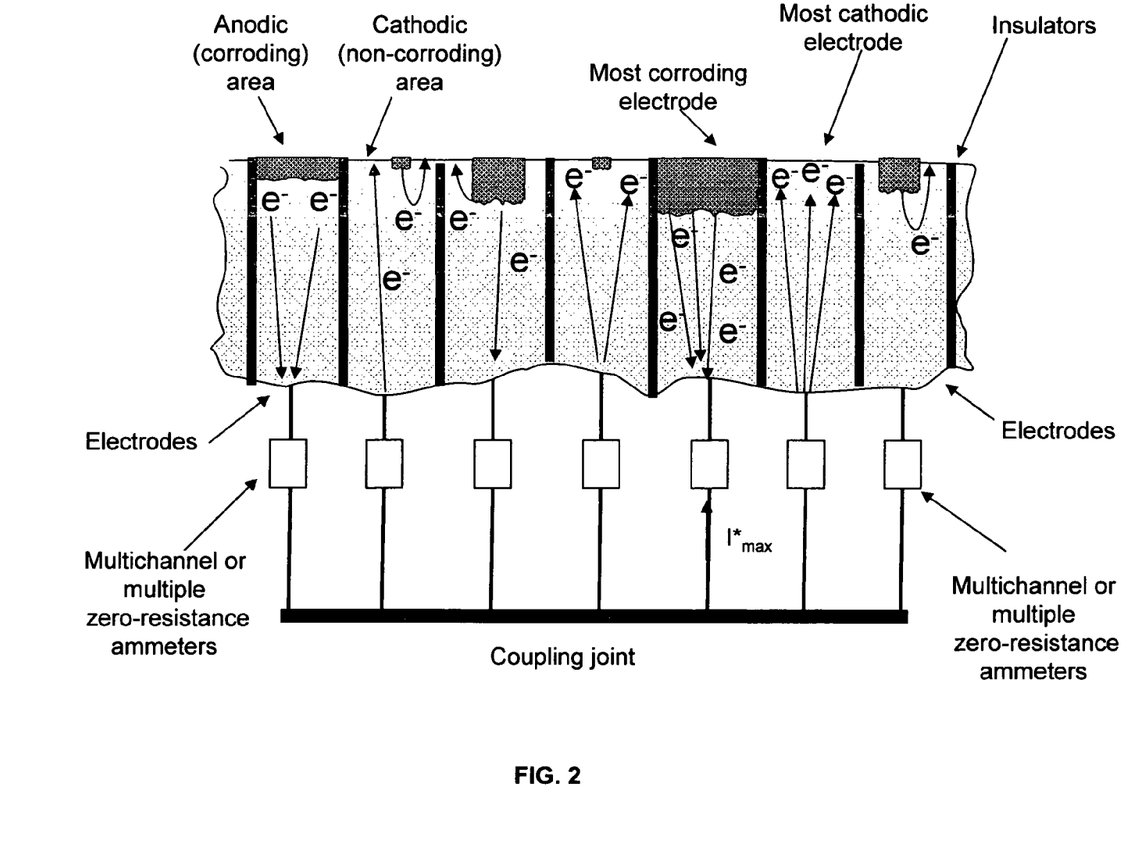
FIG. 2 illustrates the principle of a coupled multielectrode array sensor using a zero-resistance ammeter to measure the coupling currents.

FIGS. 1 and 2 show the principle of a coupled multielectrode array sensor. The multiple electrodes that are electrically isolated from each other by the insulator are connected, though resistors (FIG. 1) or zero-resistance ammeters (FIG. 2), to the coupling joint. In a corrosion environment, some electrodes may be more positive (cathodic) and some electrodes may be more negative (anodic), because of the differences in microstructures of the metal or the differences in local chemistry. The anodic electrodes would corrode and release electrons to the cathodic electrode. Because the electrodes are electrically isolated from each other, the electrons are forced to flow through the resistors or the zero-resistance ammeters in order to be measured.

The maximum anodic current—or its statistic equivalent—from a coupled multielectrode array sensor has been used to derive the maximum localized corrosion rate (the maximum penetration rate), or the cumulative localized corrosion depth (or the deepest penetration) [see L. Yang, N. Sridhar, O. Pensado and D. Dunn, "An In-situ Galvanically Coupled Multi-Electrode Array Sensor for Localized Corrosion, Corrosion, 58, 1004, 2002, and Lietai Yang, Darrell Dun and Gustavo Cragnolino, "An Improved Method for Real-time and Online Corrosion Monitoring Using Coupled Multielectrode Array Sensors," CORROSION/2005, paper no. 05379, (Houston, Tex.: NACE International, 2005)]. The following equation has been used to calculate the maximum localized corrosion rate from the maximum anodic current, $I_{max}$:

$$CR_{max} = (1/\epsilon) I_{max} W_e / (F \rho A) \quad (1)$$

Where $CR_{max}$ is the calculated maximum penetration rate (cm/s), $\epsilon$ is the current distribution factor (fraction of the electrons produced on the most corroding electrode that flows to the other electrodes through the coupling circuit), F is the Faraday constant (96485 C/mol), A is the surface area of the electrode (cm$^2$), $\rho$ is the density of the alloy of electrode (g/cm$^3$), and $W_e$ is the equivalent weight (g/mol). The value of $\epsilon$ is unity, if the most corroding electrode is significantly different from the other electrodes in the coupled multielectrode sensor probe, and close to zero, if very few of the electrons flow externally to the other electrodes.

The statistical equivalent maximum anodic current is defined as $$I^s_{max} = k\sigma + I_{mean} \quad (2)$$

where k is a constant, $\sigma$ is the standard deviation of the measured currents, and $I_{mean}$ is the mean current. The value of k varies from 2 to 4, depending on the degree of confidence and sample size (number of currents measured).

The maximum corrosion depth or penetration is related to the total damage accumulated in a given time period. The corrosion depth of the $i^{th}$ electrode may be derived from the cumulative charge that can be obtained by integrating the corrosion current through the electrode from time zero to time t:

$$Q_i = \int I_i(t) dt \quad (3)$$

where $Q_i$ is the cumulative charge of the $i^{th}$ electrode. Similarly to the maximum localized corrosion rate, the following equation has been used to calculate the maximum cumulative localized corrosion depth or penetration (cm):

$$CD_{max}=(1/\epsilon)Q_{max}W_e/(F\rho A) \quad (4)$$

where $Q_{max}$ is the maximum of the cumulative charges (coulomb) from all the electrodes, each calculated individually using Equation (3).

Figure 3:
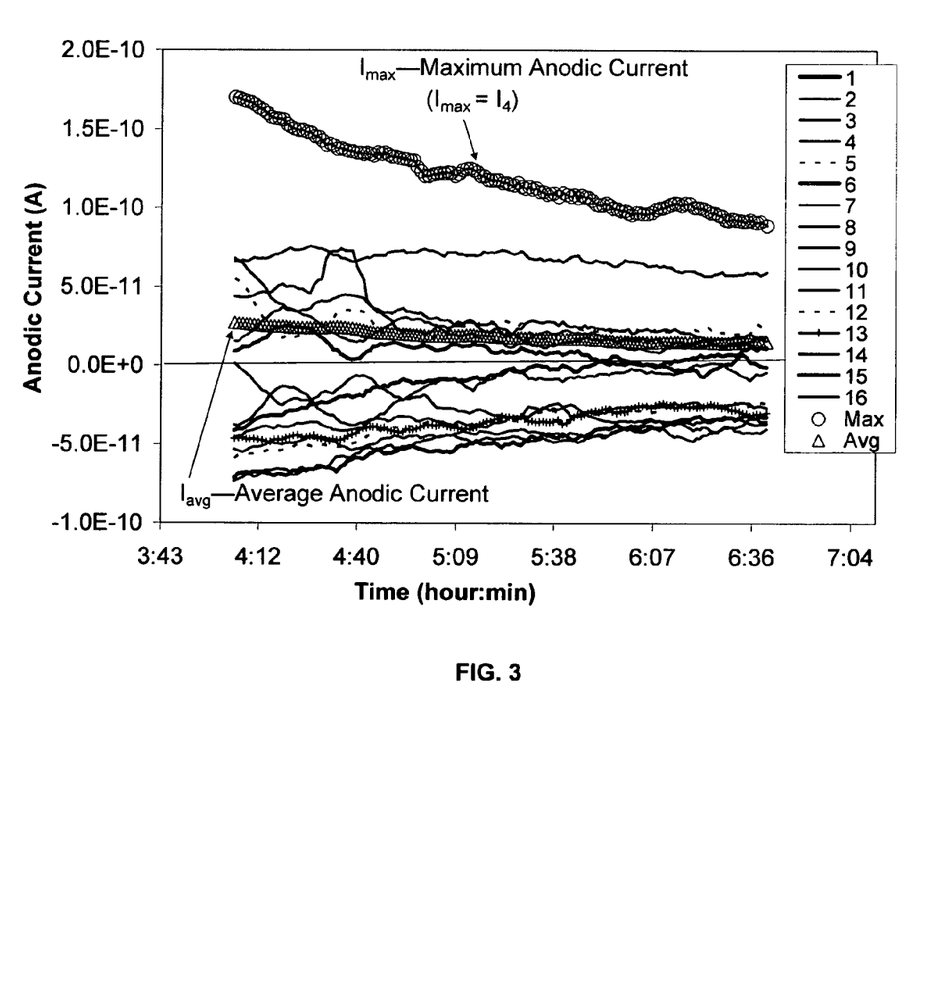
FIG. 3 illustrates typical currents measured from a stainless steel coupled multielectrode array sensor in simulated seawater.
Figure 4:
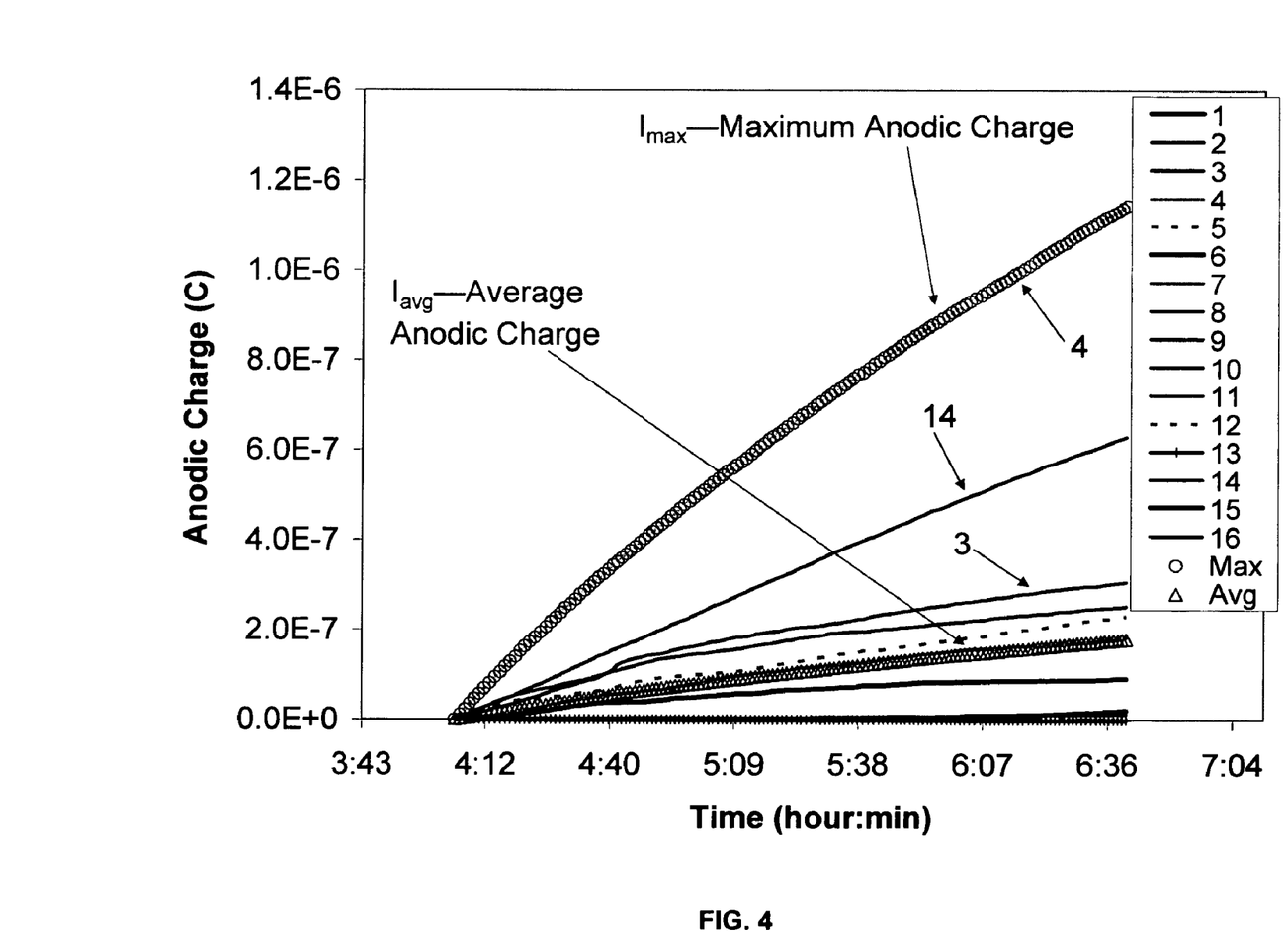
FIG. 4 illustrates the anodic charges derived from FIG. 3.
Figure 5:
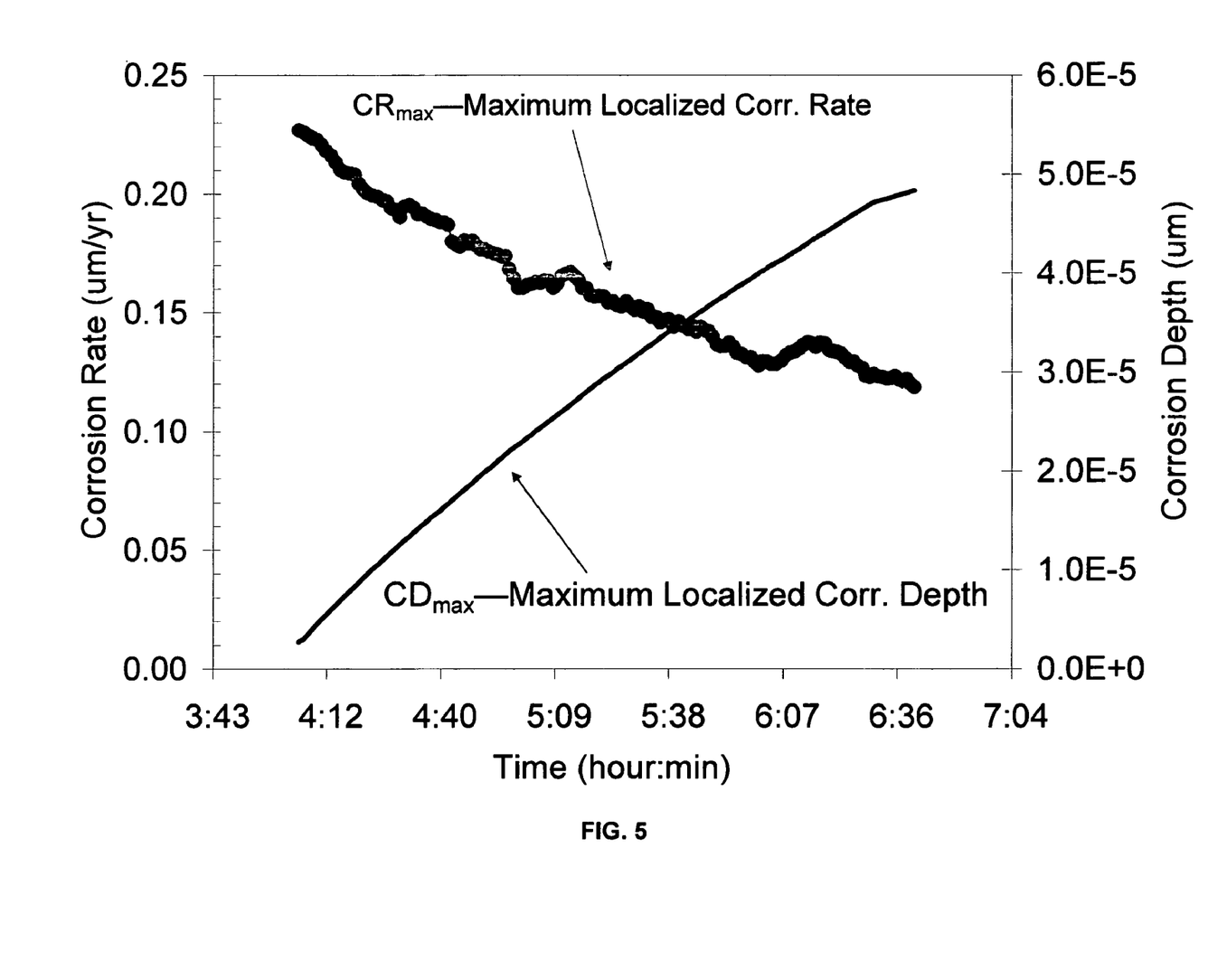
FIG. 5 illustrates the maximum localized corrosion rate and the maximum localized corrosion depth (penetration) derived from the maximum localized corrosion rate.

FIG. 3 shows the currents measured from a typical stainless steel coupled multielectrode array sensor probe in simulated seawater. The maximum anodic current was due to the current from a single electrode (Electrode #4). The anodic charges corresponding to FIG. 3 are shown in FIG. 4. The maximum localized corrosion rate and maximum corrosion depth were obtained by applying Equations (1) through (4) to the data shown in FIGS. 3 and 4, and are shown in FIG. 5. In FIG. 5, the maximum localized corrosion depth curve is the integration of the maximum localized corrosion rate curve. Because the maximum localized corrosion rate curve in FIG. 5 was from one electrode, the maximum localized corrosion rate curve and the maximum localized corrosion depth curve are directly related to each other.

Figure 6:
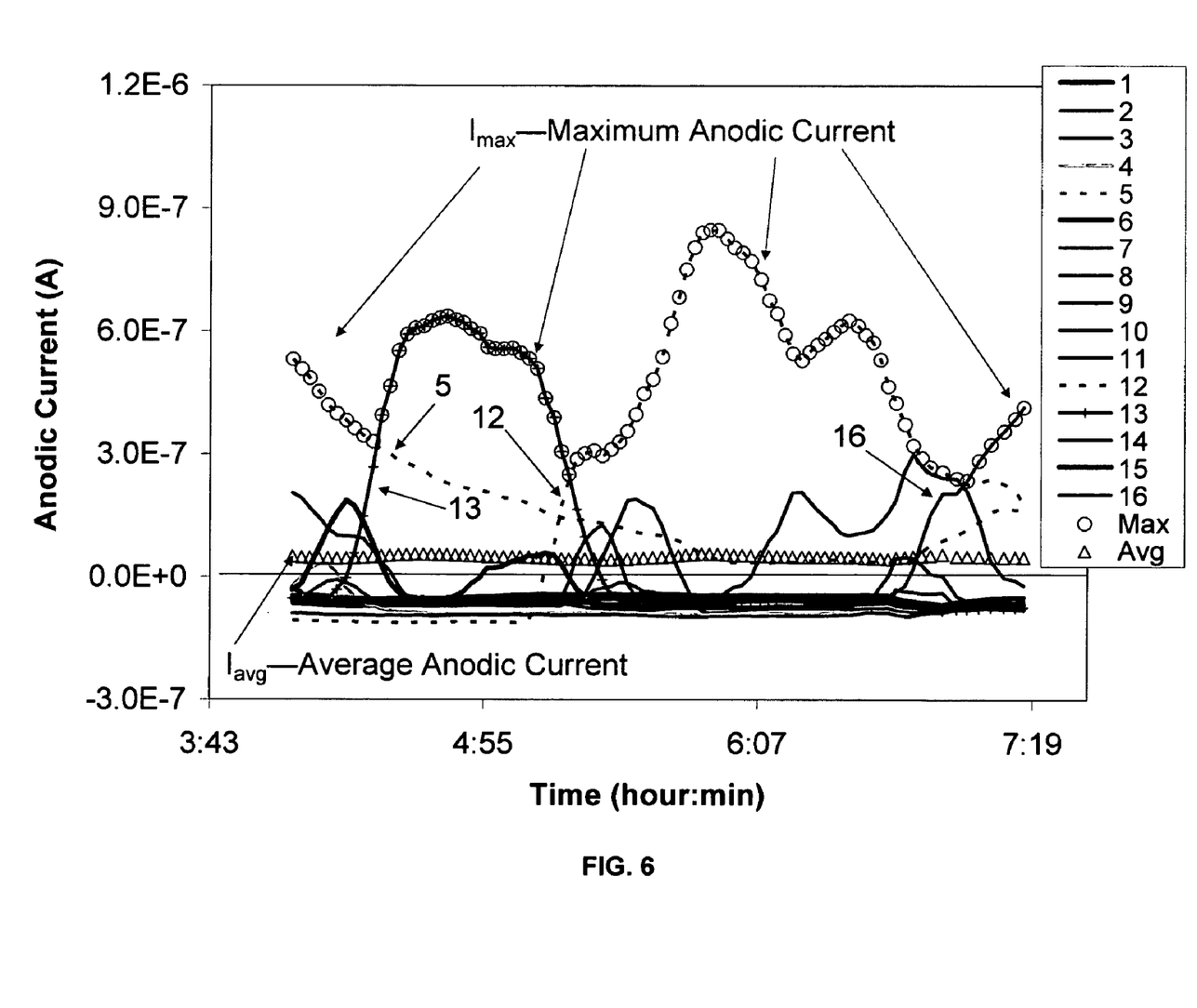
FIG. 6 illustrates typical currents measured from an aluminium coupled multielectrode array sensor in simulated seawater.
Figure 7:
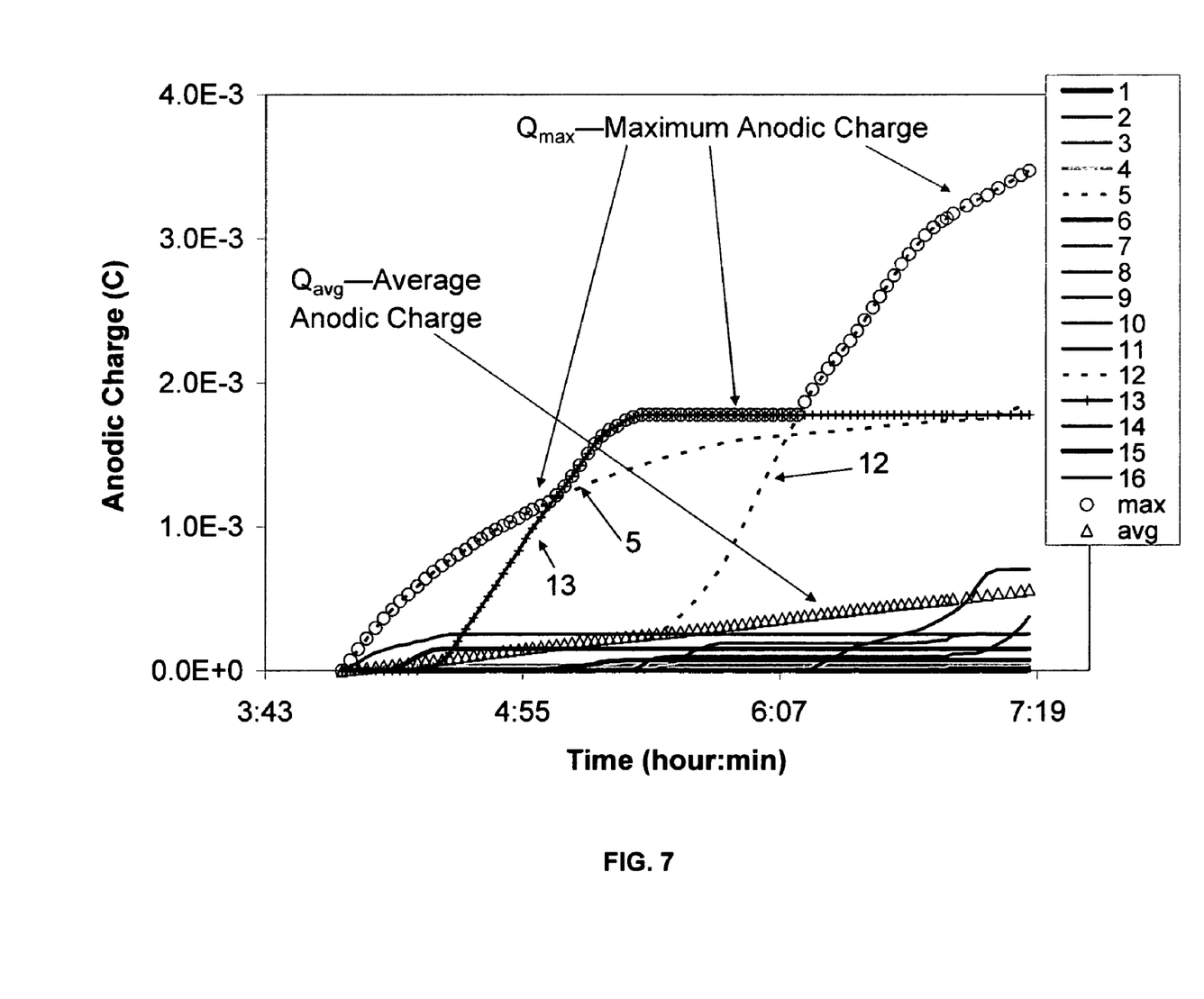
FIG. 7 illustrates the anodic charges derived from FIG. 6.
Figure 8:
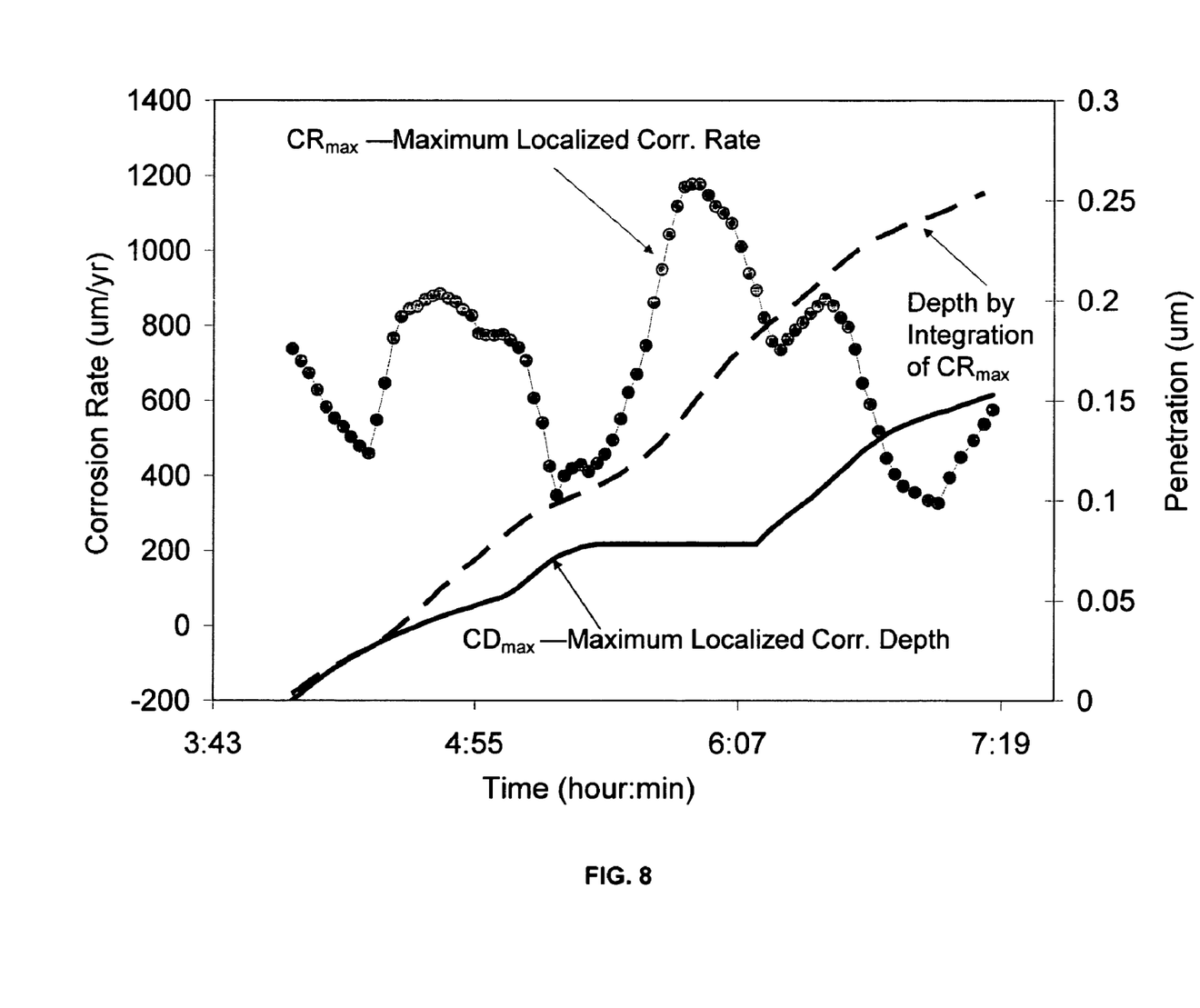
FIG. 8 illustrates the maximum localized corrosion rate, the maximum localized corrosion depth (penetration) derived from the maximum localized corrosion rate, and the actual maximum localized corrosion depth.

FIG. 6 shows the currents measured from a typical aluminium coupled multielectrode array sensor probe in simulated seawater. The maximum anodic current was measured from different electrodes (Electrodes #5, #13, #12, and #16) at different times. The anodic charges corresponding to FIG. 6 are shown in FIG. 7. The maximum localized corrosion rate and the maximum localized corrosion depth were obtained by applying Equations (1) through (4) to the data shown in FIGS. 6 and 7, and are shown in FIG. 8. Unlike FIG. 5, the actual maximum localized corrosion depth curve is not the direct integration of the maximum localized corrosion rate curve in FIG. 8. The integration of the maximum localized corrosion curves would produce a much higher depth than the actual maximum localized corrosion penetration depth, as shown in FIG. 8 (dashed line).

Cumulative Maximum Localized Corrosion Rate

Figure 9:
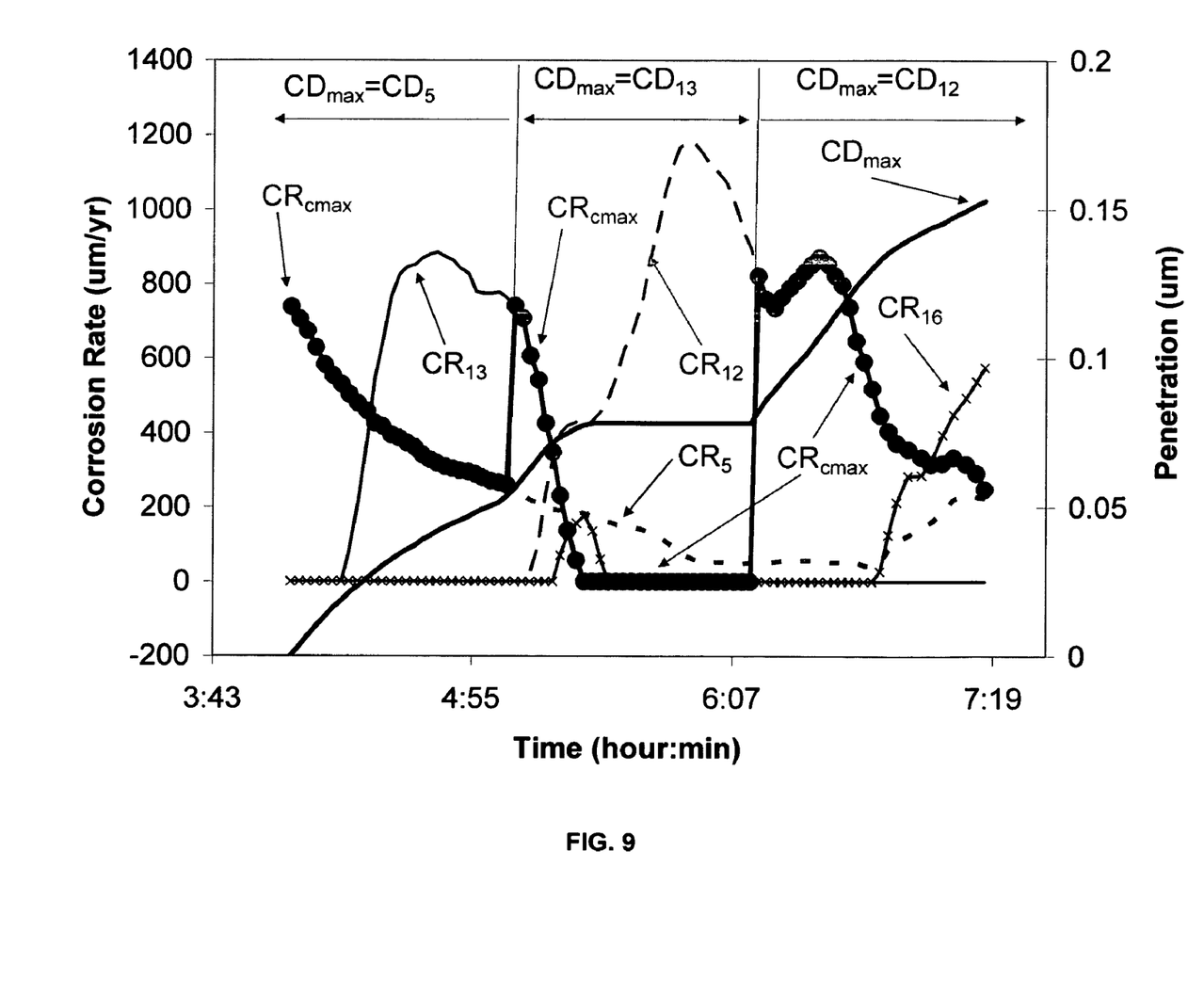
FIG. 9 illustrates the cumulative maximum localized corrosion rate ($CR_{cmax}$), corrosion rates of selected electrodes ($CR_i$, i=5, 12, 13, or 16) and maximum localized corrosion depth ($CD_{max}$).
Figure 10:
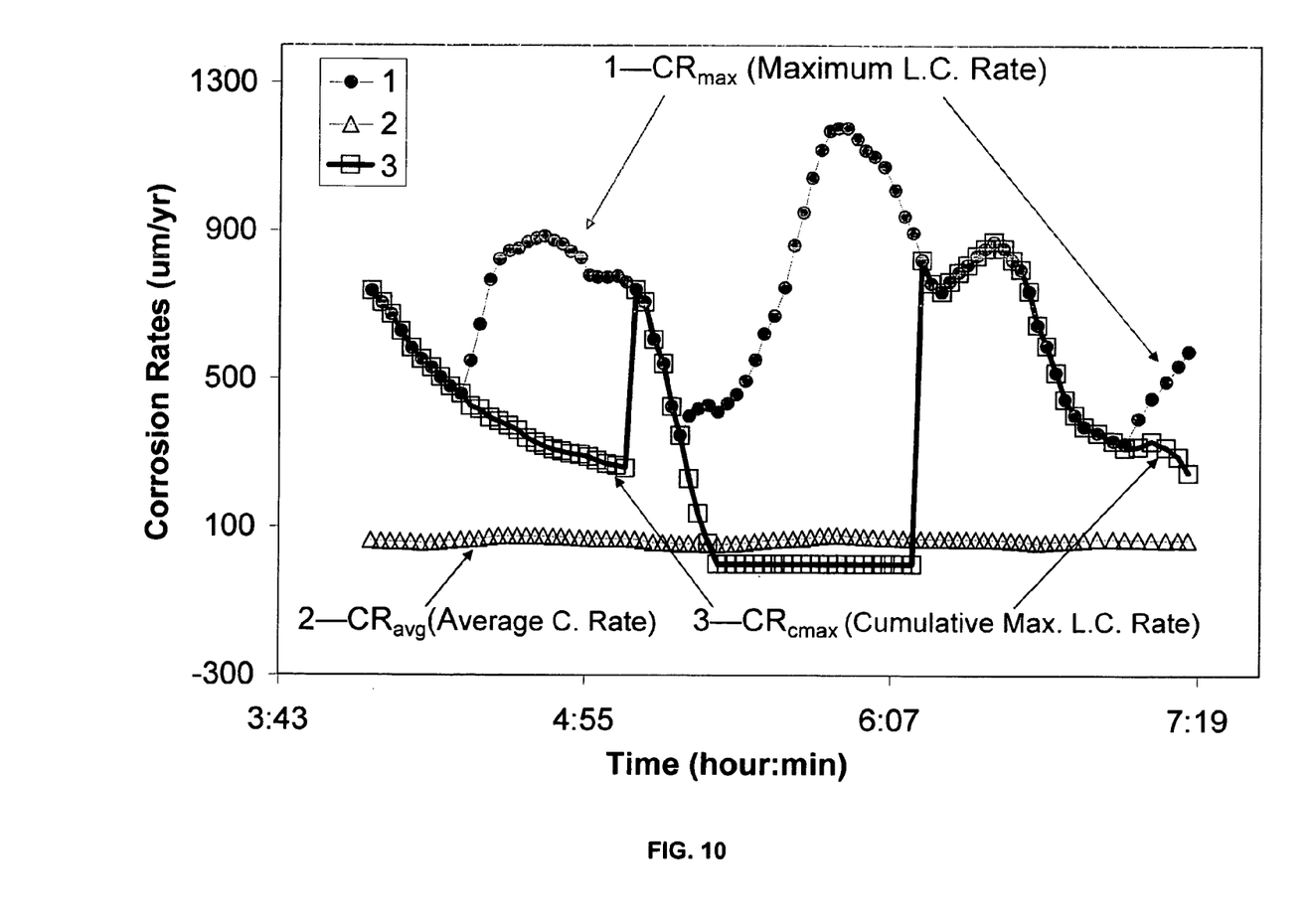
FIG. 10 illustrates the maximum localized corrosion rate, cumulative maximum localized corrosion rate, and average corrosion rate.

FIGS. 9 and 10

To solve the problem of discrepancy between the maximum localized corrosion rate and maximum localized corrosion depth, as shown in FIG. 8, a new parameter called cumulative maximum localized corrosion rate, $CR_{cmax}$, is introduced in this invention. It is defined as the derivative of the maximum localized corrosion depth curve:

$$CR_{cmax}(t)=d[CD_{max}(t)]/dt \quad (5)$$

The maximum localized corrosion depth, $CD_{max}(t)$, is proportional to the maximum anodic charge, $Q_{max}$, as shown in FIG. 7 [see Equation (4)]. The maximum anodic charge in FIG. 7 was obtained by integrating the currents from the electrodes that had the maximum anodic charge—or had been corroded the most—at time t since time zero. Therefore, the derivative of $CD_{max}(t)$ is simply a function of the current from the electrode that has the highest anodic charge at time t, $I_{max\_charge}$:

$$CR_{cmax}(t)=(1/\epsilon)I_{max\_charge}W_e/(F\rho A) \quad (6)$$

The $CR_{cmax}$ values for the data shown in FIGS. 6 and 7 are calculated and shown in FIG. 9. The maximum corrosion depth, $CD_{max}$, and the calculated corrosion rates for the electrodes that exhibited the highest corrosion currents at certain times during the test (see FIG. 6) are also plotted in FIG. 9. In the specified three time periods, the maximum localized corrosion depth equaled the values measured from Electrodes #5, #13, and #12, respectively (see FIG. 7). Therefore, the cumulative maximum localized corrosion rate, $CR_{cmax}$, was equal to the corrosion rates of these three electrodes during the different corresponding time intervals. Another way to look at the cumulative maximum localized corrosion rate is that it is the corrosion rate of the cumulatively most corroded electrode at any given time (or the electrode with the deepest pit, if the mode of localized corrosion is pitting corrosion). Because of the nature of localized corrosion, a deepest pit may be repassivated under certain conditions and the corrosion rate on this electrode may drop to zero. The zero value of $CR_{cmax}$ in the second time interval indicates that the most corroded electrode (Electrode #13) was repassivated, and the corrosion on it was stopped at a time near 6:00.

Because the cumulative maximum localized corrosion rate is simply the corrosion rate of the electrode that passed the maximum amount of charge, a sorting algorithm may be built into a real-time corrosion monitoring software to track the most corroded electrode and obtain cumulative maximum localized corrosion. The software may give the maximum localized corrosion rate, the cumulative maximum localized corrosion rate, and the average corrosion rate ($CR_{avg}$) which is calculated from the average of the anodic currents (FIG. 10). The average corrosion rate may be used to represent the general corrosion rate [see Xiaodong Sun and Lietai Yang, "Real-Time Monitoring of Localized and General Corrosion Rates in Simulated Marine Environments Using Coupled Multielectrode Array Sensors," CORROSION/2006, paper no. 06284 (Houston, Tex.: NACE, 2006)].

Because the cumulative maximum localized corrosion rate is defined as the derivative of the maximum localized corrosion depth, the $CR_{cmax}$ and $CD_{max}$ values are directly related to each other. One can solve for $CR_{cmax}$ from $CD_{max}$ by differentiation, or solve for $CD_{max}$ from $CR_{cmax}$ by integration. Unlike the maximum localized corrosion rate ($CR_{max}$), whose integration would produce an imaginary number that is often higher than the actual maximum localized corrosion depth, the integration of the cumulative maximum localized corrosion rate would produce exactly the maximum localized corrosion depth.

Figure 11:
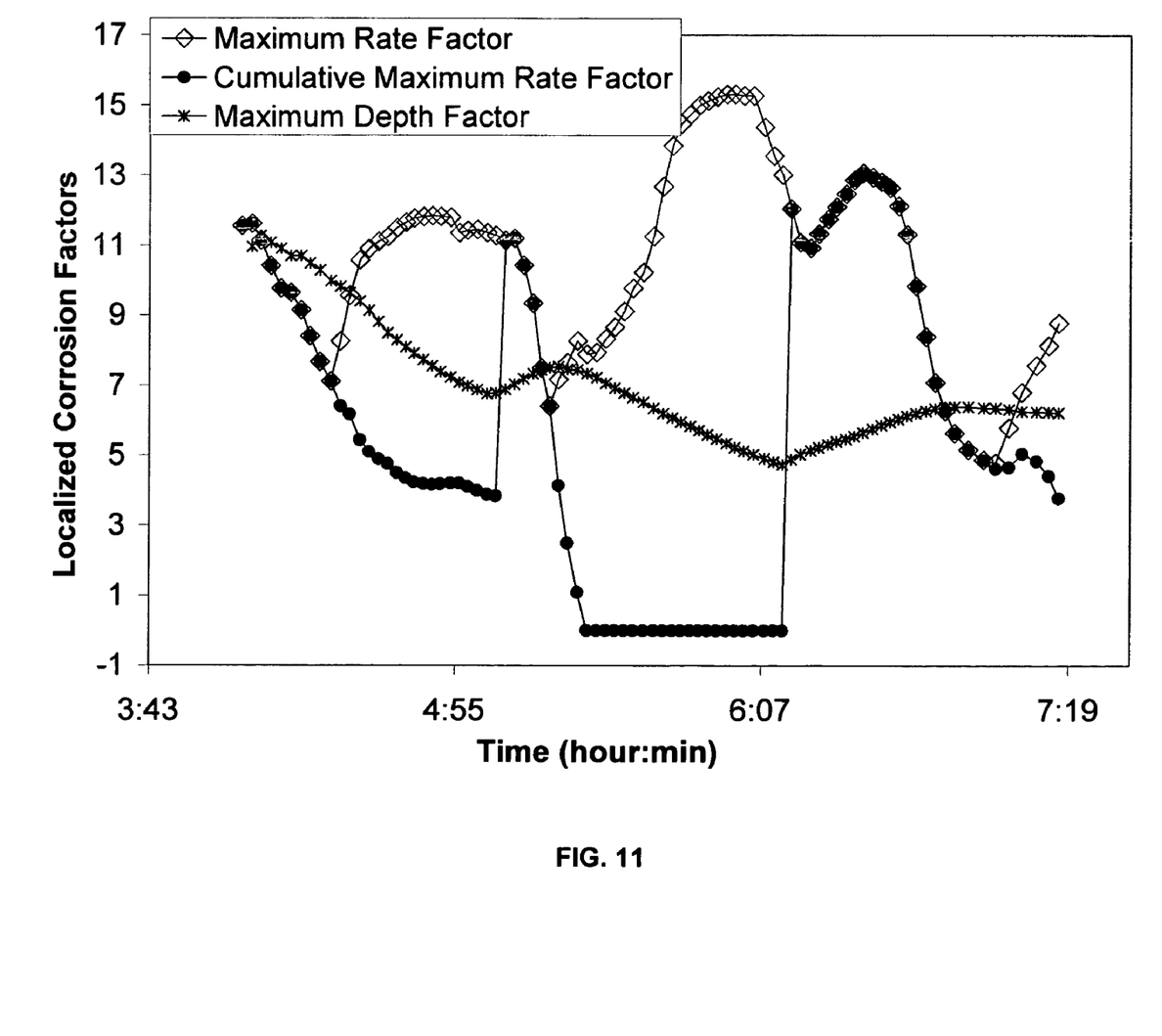
FIG. 11 illustrates the localized corrosion rate factor, cumulative localized corrosion rate factor, and localized corrosion depth factor.

FIG. 11

Localized corrosion rate factor and localized corrosion depth factor were introduced to indicate how much higher the corrosion rate on the most corroding electrode is than the average corrosion rate, and how much higher the corrosion depth on the most corroded electrode is than the average corrosion depth [see Xiaodong Sun and Lietai Yang, "Real-Time Monitoring of Localized and General Corrosion Rates in Simulated Marine Environments Using Coupled Multielectrode Array Sensors," CORROSION/2006, paper no. 06284 (Houston, Tex.: NACE, 2006)].

Similarly, cumulative localized corrosion rate factor $f_{crate}$ is defined here to indicate how much higher or lower the cumulative maximum localized corrosion rate is than the average corrosion rate:

$$f_{crate}=CR_{max}/CR_{avg} \quad (7)$$

FIG. 11 shows the cumulative localized corrosion rate factor, localized corrosion rate factor, and localized corrosion depth factor for the data shown in FIGS. 8 and 9.

Figure 12:
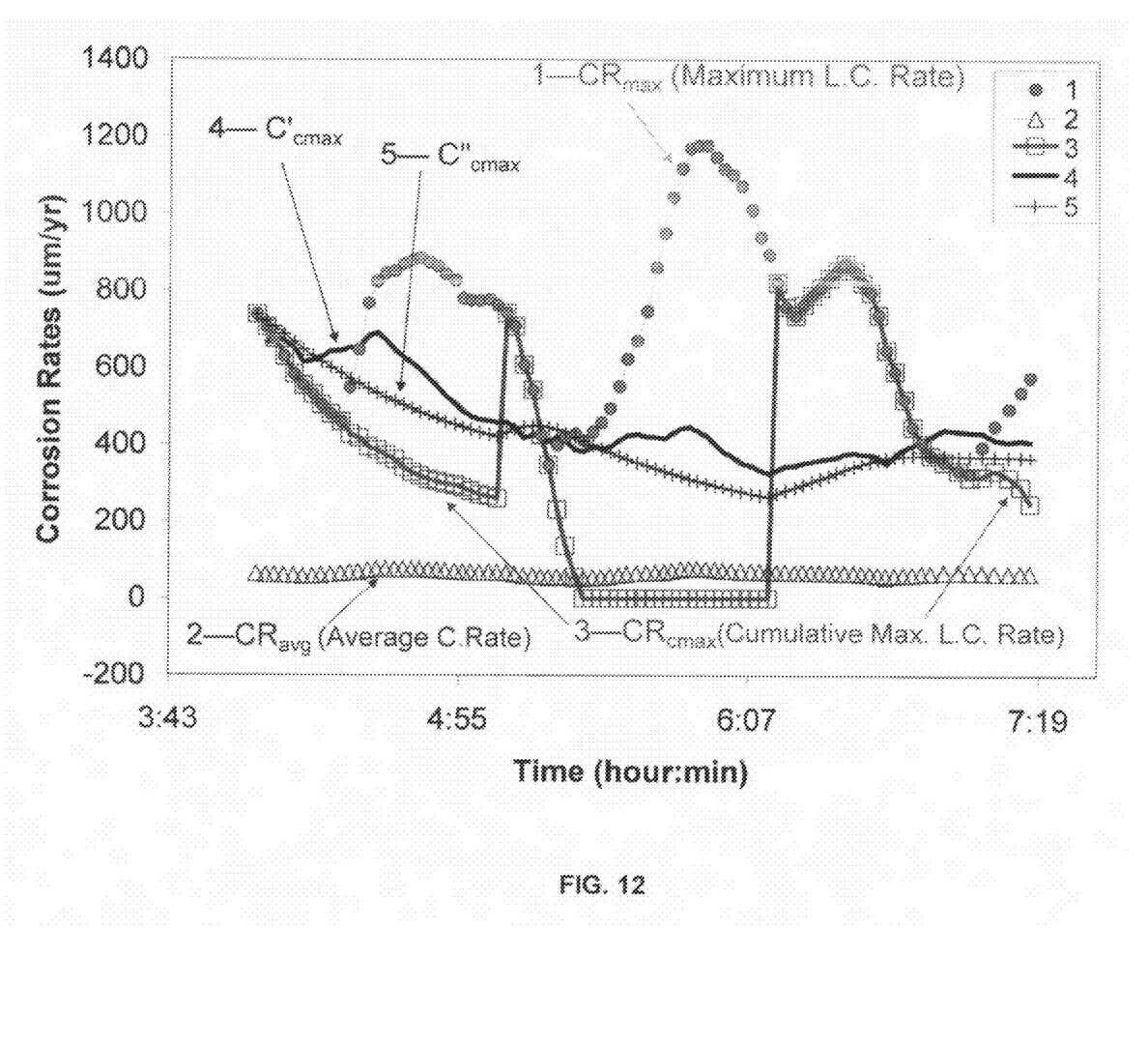
FIG. 12 illustrates alternative representations of cumulative localized corrosion rate by the localized corrosion depth factor multiplied by average corrosion rate or by time-averaged cumulative maximum localized corrosion rate.

FIG. 12

Although the cumulative maximum localized corrosion rate, as shown in FIGS. 9 and 10, reflects the true corrosion process of the most corroded electrode, it is not a continuous function. Sometimes it may be extremely high, but other times it may be zero. When it is equal to zero, individuals may be misled into thinking that localized corrosion is not happening. To avoid the tendency of having the cumulative maximum localized corrosion rate mislead individuals, other alternatives may be used to approximate the cumulative maximum localized corrosion rate. Examples of the approximations are:

$$CR'_{cmax} = \frac{1}{t}\sum CR_{cmax}(t_i)\Delta t_i, \; i \text{ from } 1 \text{ to } n \qquad (8)$$

or, $$CR'_{cmax} = \frac{1}{t}\int_0^t CR_{cmax}(t)\,dt \qquad (9)$$

and, $$CR''_{cmax} = f_{depth}CR_{avg} \qquad (10)$$

where $$f_{depth} = Q_{max}/Q_{avg} \qquad (11)$$

In Equations (10) through (11), $Q_{avg}$ is the average anodic charge, and $f_{depth}$ is the localized corrosion depth factor. $Q_{avg}$ is calculated by dividing the sum of the individual anodic charges obtained with Equation (3) by the number of electrodes or the number of the anodic electrodes [see Xiaodong Sun and Lietai Yang, "Real-Time Monitoring of Localized and General Corrosion Rates in Simulated Marine Environments Using Coupled Multielectrode Array Sensors," CORROSION/2006, paper no. 06284 (Houston, Tex.: NACE, 2006)]. Hence, $CR'_{cmax}$ represents the cumulative maximum localized corrosion rate averaged over a period from time zero to time t (or called time-averaged cumulative maximum localized corrosion rate), and $CR''_{cmax}$ represents the average corrosion rate multiplied by the localized corrosion depth factor. Both $CR'_{cmax}$ and $CR''_{cmax}$ are plotted, along with $CR_{max}$, $CR_{cmax}$, and $CR_{avg}$, in FIG. 12. It should be noted that neither the integration of the $CR'_{cmax}$ nor the integration of $CR''_{cmax}$ will produce a value that would equal the maximum localized corrosion depth.

The localized corrosion depth factor can also be calculated using the following equation:

$$f_{depth} = CD_{max}/CD_{avg} \qquad (12)$$

where $CD_{avg}$ is the average corrosion depth. The relationship between $CD_{avg}$ and $Q_{avg}$ is the same as Equation (4).

Cumulative Average Corrosion Rate

As mentioned above, the cumulative maximum localized corrosion rate is significantly different from the maximum localized corrosion rate, if the maximum localized corrosion rate is not due to the same electrode. However, the cumulative average corrosion rate and the average corrosion rate are the same. This is illustrated as follows:

Based on the definition of the cumulative maximum corrosion rate, the cumulative average corrosion rate $CR_{cavg}$ may be written as:

$$CR_{cavg}(t) = dCD_{avg}(t)/dt \qquad (13)$$

$$CR_{cavg}(t) = d[\int CR_{avg}(t)dt]/dt \qquad (14)$$

$$CR_{cavg}(t) = CR_{avg}(t) \qquad (15)$$

OTHER EMBODIMENTS

Although the present invention has been described in detail, it should be understood that various changes, substitutions, and alterations can be made hereto without departing from the spirit and scope of the invention as defined by the appended claims.

The invention claimed is:

1. A method of using a multielectrode sensor to measure localized corrosion, comprising:
   (a) exposure of the sensor to the corrosion environment of interest;
   wherein the sensor has an array of substantially similar metallic electrodes arranged such that each electrode has a surface area operable to be exposed to the corrosion environment, and such that each electrode is electrically insulated from other electrodes;
   wherein each electrode is operable as an anode or cathode, depending on the electrochemical property of that electrode;
   wherein each electrode is connected to a coupling joint, such that the collection of the electrodes simulates a one-piece electrode surface;
   (b) measurement of the anodic or cathodic current from each electrode to the coupling joint;
   (c) calculation of the anodic charge for each electrode by integrating the anodic current passing through the electrode;
   (d) calculation of the cumulative maximum localized corrosion rate using the anodic current from the electrode that has the maximum anodic charge.

2. The method of claim 1, wherein the electrodes are each connected to the coupling joint through a resistor.

3. The method of claim 1, wherein the electrodes are each connected to the coupling joint through a zero-resistance ammeter.

4. The method of claim 1, wherein the degree of localized corrosion is represented by the ratio of the cumulative maximum localized corrosion rate to the average corrosion rate, which is calculated using the average of the anodic currents.

5. The method of claim 1, wherein the cumulative maximum localized corrosion rate is approximated by averaging it over a time period.

\* \* \* \* \*